United States Patent
Van Der Mooren et al.

(10) Patent No.: US 8,696,119 B2
(45) Date of Patent: Apr. 15, 2014

(54) SYSTEMS AND METHODS FOR DETERMINING INTRAOCULAR LENS POWER

(75) Inventors: Marrie H. Van Der Mooren, Engelbert (NL); Carmen Canovas Vidal, Groningen (NL); Patricia Ann Piers, Groningen (NL)

(73) Assignee: AMO Groningen B.V., Groningen (NL)

( * ) Notice: Subject to any disclaimer, the term of this patent is extended or adjusted under 35 U.S.C. 154(b) by 5 days.

(21) Appl. No.: 13/458,446

(22) Filed: Apr. 27, 2012

(65) Prior Publication Data
US 2012/0274895 A1  Nov. 1, 2012

Related U.S. Application Data

(60) Provisional application No. 61/480,589, filed on Apr. 29, 2011.

(51) Int. Cl.
*G02C 7/02* (2006.01)
*G02C 7/04* (2006.01)
*A61F 2/16* (2006.01)

(52) U.S. Cl.
USPC ............... 351/159.74; 623/6.11; 351/159.73

(58) Field of Classification Search
USPC ........... 351/159.74, 159.78, 159.79; 623/6.11, 623/6.22–6.29, 6.36
See application file for complete search history.

(56) References Cited

U.S. PATENT DOCUMENTS 5,092,880 A * 3/1992 Ohmi ........................ 623/6.23
2009/0251664 A1 10/2009 Norrby et al.

OTHER PUBLICATIONS

Eibschitz-Tsimhoni M., et al., "Intraocular Lens Power Calculation in Children," Survey of Ophthalmology, 2007, vol. 52 (5), pp. 474-482.
International Search Report and Written Opinion for Application No. PCT/US2012/035539, mailed on Aug. 13, 2012, 15 pages.
Norrby et al., "Prediction of intraocular lens power using the lens haptic plane concept," J. Cataract Refract. Surg, pp. 254-259, 1997, vol. 23 (2).
Norrby S., et al., "Clinical Application of the Lens Haptic Plane Concept with Transformed Axial Lengths," Journal of Cataract and Refractive Surgery, 2005, vol. 31 (7), pp. 1338-1344.
Olsen T., "Prediction of the Effective Postoperative (Intraocular Lens) Anterior Chamber Depth," Journal of Cataract and Refractive Surgery, 2006, vol. 32 (3), pp. 419-424.
Retzlaff J., "A New Intraocular Lens Calculation Formula," Journal—American Intra-Ocular Implant Society, 1980, vol. 6 (2), pp. 148-152.
Norrby S., et al., "Sources of Error in Intraocular Power Calculation," Journal of Cataract & Refractive Surgery , 2008, vol. 34 (3), pp. 368-376.
Olsen T., "Calculation of Intraocular Lens Power: A Review," Acta Ophthalmologica Scandinavica, 2007, vol. 85, pp. 472-485.

* cited by examiner

*Primary Examiner* — Evelyn A Lester
*Assistant Examiner* — William Alexander
(74) *Attorney, Agent, or Firm* — AMO Groningen B.V.

(57) ABSTRACT

The present invention relates to devices, systems and methods for determination or selection of a lens power based on the postoperative vitreous length of an eye. The combined measurements of $VL_{pre}$, $ACD_{pre}$, AL, and/or LT are highly predictive in calculating the postoperative vitreous length, from which the position of the implanted intraocular lens or optic can be derived, and then selection of the appropriate lens power.

14 Claims, 5 Drawing Sheets

Figure 4 Predicted versus observed vitreous length

SYSTEMS AND METHODS FOR DETERMINING INTRAOCULAR LENS POWER

BACKGROUND OF THE INVENTION

1. Field of the Invention

The present invention relates generally to ocular surgical procedures involving implantable lenses, and more specifically to devices, systems and methods for the determination or selection of a lens power for providing emmetropic vision or, if chosen, a specific ametropic vision, taking into account various parameters of the eye.

2. Description of the Related Art

Intraocular Lenses (IOLs) may be used for restoring visual performance after a cataract or other ophthalmic procedure in which the natural crystalline lens is replaced with or supplemented by implantation of an IOL. Accurate determination of lens power is an important aspect in providing emmetropia, or a desired degree of ametropia. Measurements of the eye are typically made preoperatively and a lens power is selected based on correlations between the measured values and lens powers providing a desired refractive outcome.

Over the years a number of intraocular lens power calculation formulas have been developed, for example, as discussed in the book published by SLACK Incorporated entitled *Intraocular Lens Power Calculations*, by H. John Shammas. These power formulas may be broadly characterized into at least two categories: theoretical formulas, which are based on a geometric optic, two-lens vergence formula; and regression formulas, which are based on regression formulas obtained by fitting data from a large patient database to an equation relating lens power to one or more parameters thought to correlate with lens power. While progress has been made in the accuracy of intraocular lens power calculation formulas to obtain better refractive outcomes, undesirable refractive outcomes due to improper intraocular lens power calculations still occur. Apart from the general desire for spectacle-free refractive outcomes, demands for more accurate lens power calculation have also increased due to the introduction of multifocal, as well as accommodating IOLs.

Many of the current formula algorithms were derived by optical back-calculations to agree with a refractive outcome. In this manner they may be confounded with errors in all parameters used in the calculation, and the oversimplification of thin-lens theory. An evaluation of the sources of errors in lens power calculations was published by Sverker Norrby entitled "Sources of error in intraocular lens power calculation", *Journal of Cataract and Refractive Surgery*, Vol. 34, pp. 368-376, March 2008. In this paper, preoperative estimation of postoperative intraocular lens position was determined to be the largest contributor of error in the refractive outcome of cataract surgery, with an error contribution of 35%, relative to all error sources evaluated. Another publication by Olson ("Calculation of intraocular lens power: a review." *Acta Opthalmologica Scandinavica* 2007; 85:472-485) reports the same order of magnitude for the same source of error.

In most, if not all of the current formula algorithms, there are a number of ocular parameters that are used in deriving an appropriate lens power for implantation into the eye. These parameters include axial length (AL), corneal radius (CR) or power (K), and anterior chamber depth prior to surgery ($ACD_{pre}$), among others. In general, one or more of these parameters are used to provide the preoperative estimation of the postoperative effective lens position (ELP), which is related to the IOL's principal plane, although it may be modified depending on the surgeon through the optimization of the corresponding IOL constant. The ELP is then used in combination with one or more of these same parameters to provide an estimate of the correct lens power to provide a desired refractive outcome (typically emmetropia).

For example, in the SRK/T method, the empirical calculation based on regressions is used to predict the ELP in the eye after surgery. Once that position is known, the IOL power to implant is calculated by simple paraxial optics, taking into account that the eye is a two lens system (cornea+IOL), focusing on the retina. This approach is based on Fyodorov's theoretical formula. However, as discussed above, calculating ELP is a large error source in this process. Accordingly, better systems and methods are needed that will allow reliable and accurate determination of an implanted lens' power.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

DETAILED DESCRIPTION OF THE DRAWINGS

The present invention generally provides devices, systems, and methods for selecting ophthalmic lenses and/or an optical power for such lenses that will provide a predetermined refractive outcome. In many cases the desired outcome will be emmetropia, for example, so that the eye into which the lens is located has a visual acuity for distant objects that is at least 20/20 based on a Snellen chart.

The following disclosure will be primarily directed to embodiments of the invention as they apply to implantable intraocular lenses; however, it is understood that other embodiments may be applied directly, or indirectly, to other types of ophthalmic lenses including, but not limited to, corneal implants, corneal surgical procedures such as LASIK or PRK, contact lenses, and other such devices. In some embodiments, various types of ophthalmic devices are combined, for example, an intraocular lens and a LASIK procedure may be used together to provide a predetermined visual outcome. Embodiments of the invention may also find particular use with multifocal or accommodating intraocular lenses, where a proper selection of lens power may be particularly important for achieving a desired refractive outcome.

Figure 1:
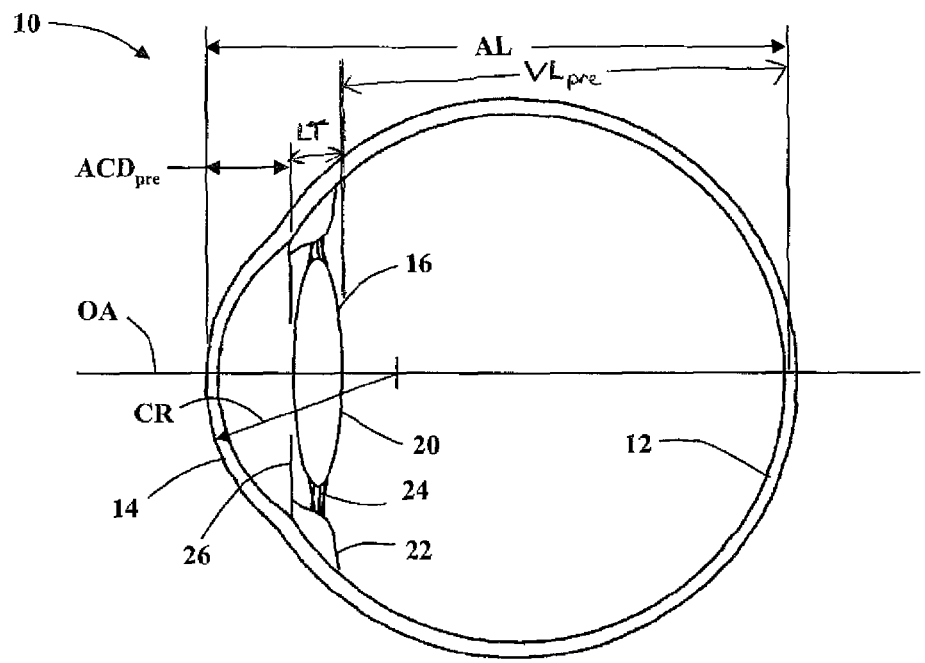
FIG. 1 is a cross-sectional view of a phakic eye containing a natural crystalline lens.

Embodiments of the invention may be understood by reference to FIG. 1, which is a cross-sectional view of a phakic eye with the natural crystalline lens, an eye 10 comprises a retina 12 that receives light in the form of an image that is produced by the combination of the optical powers of a cornea 14 and a natural crystalline lens 16, both of which are generally disposed about an optical axis OA. As used herein, an "anterior direction" is in the direction generally toward the cornea 14, while a "posterior direction" is generally in the direction toward the retina 12.

The natural lens 16 is contained within a capsular bag 20, which is a thin membrane that completely encloses the natural lens 16 and is attached to a ciliary muscle 22 via zonules 24. An iris 26, disposed between the cornea 14 and the natural lens 16, provides a variable pupil that dilates under lower lighting conditions (scotopic vision) and contracts under brighter lighting conditions (photopic vision). The ciliary muscle 22, via the zonules 24, controls the shape and position of the natural lens 16, which allows the eye 10 to focus on both distant and near objects. Distant vision is provided when the ciliary muscle 22 is relaxed, wherein the zonules 24 pull the natural lens 16 so that the capsular bag 20 is generally flatter and has a longer focal length (lower optical power). Near vision is provided as the ciliary muscle contracts, thereby relaxing the zonules 24 and allowing the natural lens 16 to return to a more rounded, unstressed state that produces a shorter focal length (higher optical power).

The optical performance of the eye 10 also depends on the spacing between the cornea 14 and the natural lens 16, sometimes referred to as the anterior chamber depth prior to an ocular surgical procedure, $ACD_{pre}$. As used herein, the "anterior chamber depth prior to surgery", "anterior chamber depth prior to an ocular surgical procedure", or "$ACD_{pre}$", is defined as a distance between an apex of the anterior corneal surface and an apex of the anterior natural crystalline lens surface, prior to a surgery to replace the natural crystalline lens 16 with an intraocular lens. In some situations or cases, $ACD_{pre}$ may be defined or approximated as a distance between an apex of a cornea and an anterior surface of the iris 26.

Figure 2:
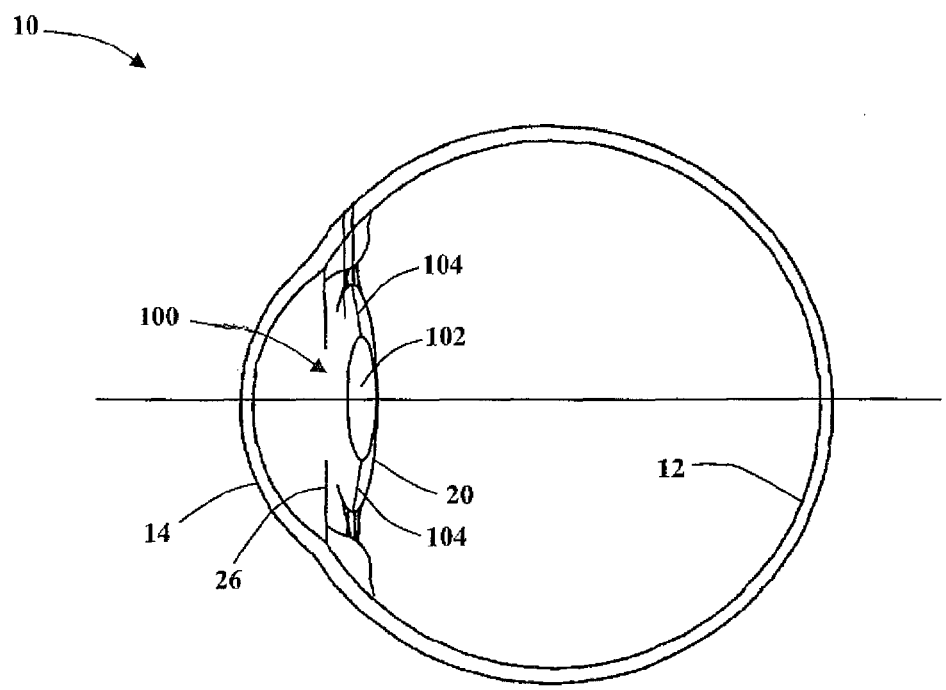
FIG. 2 is a cross-sectional view of a pseudophakic eye containing an intraocular lens.

Referring additionally to FIG. 2, which is a cross-sectional view of a pseudophakic eye 10, the natural crystalline 16 lens has been replaced by an intraocular lens 100 according to an embodiment of the present invention. The intraocular lens 100 comprises an optic 102 and haptics 104, the haptics 104 being generally configured to center the optic 102 within the capsular bag 20. Numerous configurations of haptics 104 relative to optic 102 are well know within the art and embodiments of the present invention may be applied to any of these.

In order to calculate, determine, or estimate the power of an intraocular lens 100 that is able to provide emmetropia or some other predetermined refractive outcome, various dimensions or measurements of the eye 10 are made prior to the surgical procedure. In addition to $ACD_{pre}$, embodiments of the present invention also measure axial length AL, and/or natural lens thickness LT, as illustrated in FIG. 1. From these measurements, $VL_{pre}$, which is the preoperative vitreous length of the eye measured as the difference between the AL and the $ACD_{pre}$ plus LT can be ascertained.

Various formulations exist within the art that are used for calculation both of lens power and position of an intraocular lens after an ocular surgical procedure. These formulations generally comprise three steps:

1. Measure an eye;
2. Estimate the postoperative position of an intraocular lens;
3. Perform a lens power calculation based on the estimate and/or eye measurements.

Although all three steps are important, the second step of estimating the postoperative position of an intraocular lens may benefit most from improvements in the current state of the measurement arts. For example, in the Norrby reference cited above, preoperative estimation of the ELP was determined to be the largest contributor of error in the refractive outcome of cataract surgery, with an error contribution of 35%, relative to all error sources evaluated. In addition, the correct determination of the actual lens position is even more important because it is a real distance, and not a manufactured parameter that may be modified to optimize outcomes.

Furthermore, the inventors have found that the combined measurements of $VL_{pre}$, $ACD_{pre}$, and LT are highly predictive in calculating the postoperative vitreous length, from which the position of the implanted intraocular lens 100 or optic 102 can be derived if its thickness is known. The calculated position will generally be given herein in terms of the "postoperative vitreous length" ($VL_{post}$), which is defined herein as the distance from the back of the IOL to the retina.

In certain embodiments, a highly predictive formulation of $VL_{post}$ is calculated based on the following mathematical relationship which includes $VL_{pre}$, $ACD_{pre}$, and LT:

$$VL_{post}=C1+C2*VL_{pre}+C3*ACD_{pre}+C4*LT, \quad (1)$$

where $VL_{pre}$ is the preoperative vitreous length of the eye measured as the difference between the AL and the $ACD_{pre}$ plus LT. $ACD_{pre}$ is the anterior chamber depth prior to an ocular surgical procedure as measured from the anterior corneal surface to the anterior lens surface, LT is the lens thickness, and C1-C4 are constants, that may depend on the IOL model. AL, $ACD_{pre}$ and LT may be measured with, for example the AC Master or other biometer and $VL_{pre}$ can be then be calculated from these measurements.

By way of non-limiting example, in certain 3 piece intraocular lens embodiments, constants for $VL_{post}$ may be as follows: C1=−0.901; C2=0.982; C3=0.309; and C4=0.545.

Figure 3:
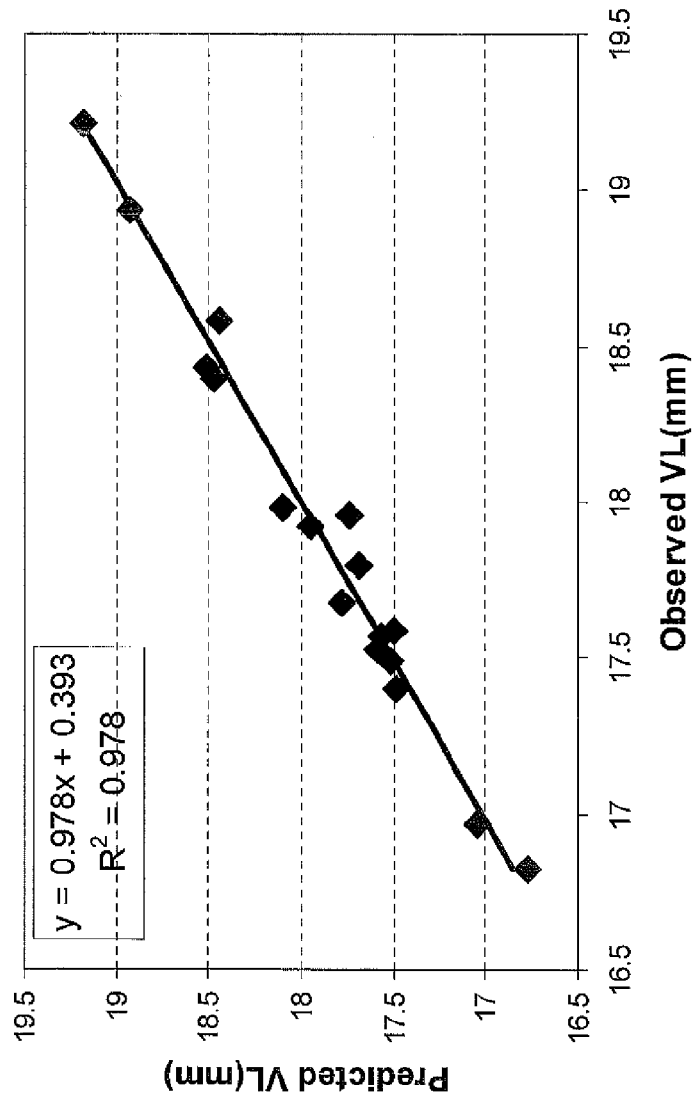
FIG. 3 is a graph illustrating the predicted versus observed vitreous length, using the preoperative vitreous length, ACD and lens thickness as parameters.

This prediction was checked post-operatively by measuring the $ACD_{post}$ with the AC master, and then calculating the actual $VL_{post}$ as equaling AL−($ACD_{post}$+$IOL_{ct}$) where $IOL_{ct}$ is the center thickness of the implanted IOL. This illustrated embodiment was found to be highly predictive of $VL_{post}$ with $r^2$=0.978, as illustrated in FIG. 3.

Figure 4:
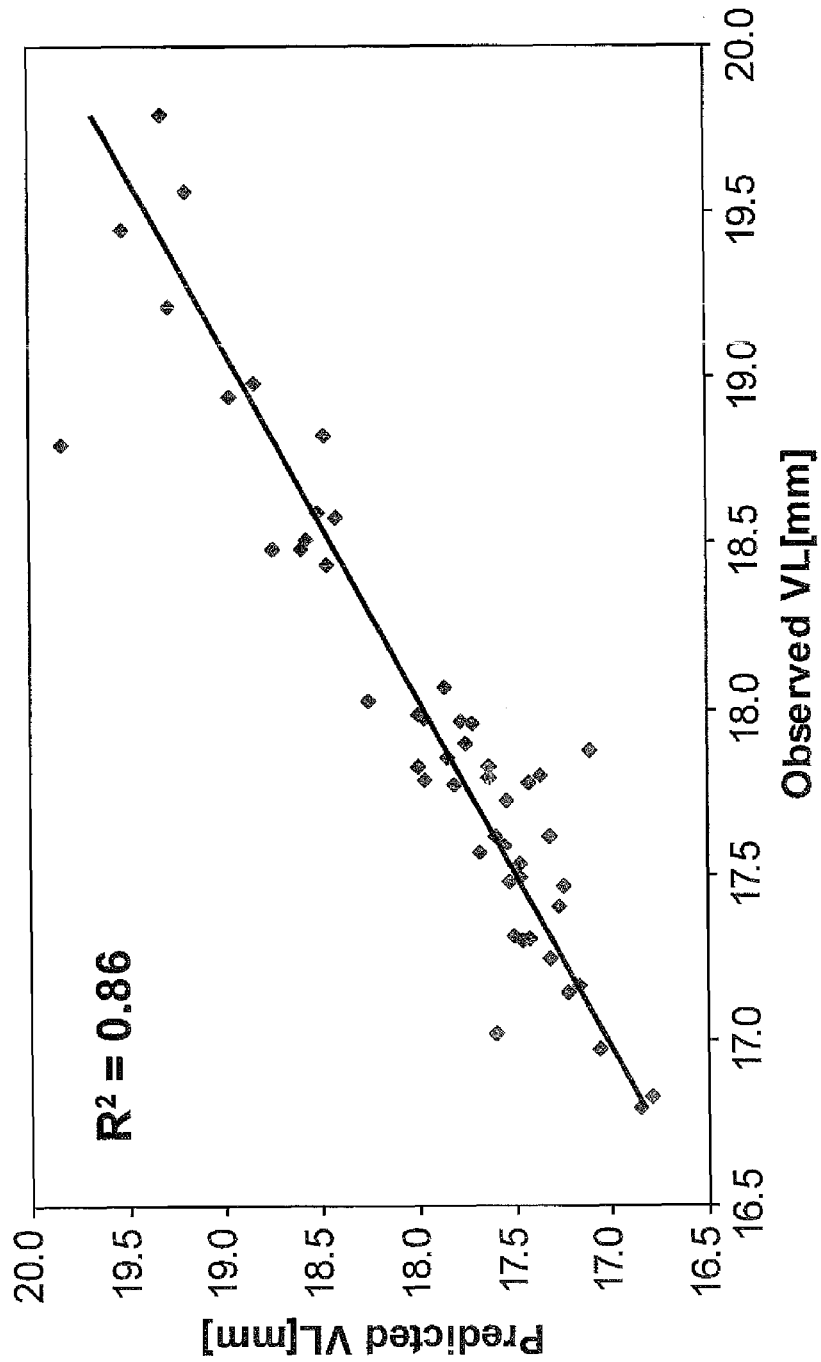
FIG. 4 is a graph illustrating the predicted versus observed vitreous length, using the preoperative vitreous length and lens thickness as parameters.

In some embodiments, AL may be used rather than $VL_{pre}$ according to the following mathematical relationship: $VL_{post}$=AL−($ACD_{pre}$+0.5LT). AL may be measured, for example, with the IOL Master. This illustrated embodiment was found to be highly predictive of $VL_{post}$ with $r^2$=0.86 as seen in FIG. 4.

Another embodiment uses AL rather than $VL_{pre}$ according to the following mathematical relationship: $VL_{post}$=C1+C2*AL+C3*$ACD_{pre}$+C4*LT where constants in certain 1 piece intraocular lens embodiments may be as follows: C1=−2.042; C2=0.944; C3=0.396; and C4=0.203. This illustrated embodiment was found to be highly predictive of $VL_{post}$ with $r^2$=0.93. By way of non-limiting example, in certain 3 piece intraocular lens embodiments, constants for $VL_{post}$ may be as follows: C1=−0.902; C2=0.983; C3=0.673; and C4=0.437. This illustrated embodiment was also found to be highly predictive of $VL_{post}$ with $r^2$=0.98.

In some embodiments, one or more of the measured variables may be left out. For example, the measurement of $ACD_{pre}$ may be left out and the coefficients for LT and $VL_{pre}$ may be evaluated according to the following mathematical relationship:

$$VL_{post}=-C1+C2*VL_{pre}+C3*LT$$

where C1=1.63, C2=0.912, and C3=0.448. This illustrated embodiment was also found to be highly predictive of $VL_{post}$ with $r^2$=0.86.

Figure 5:
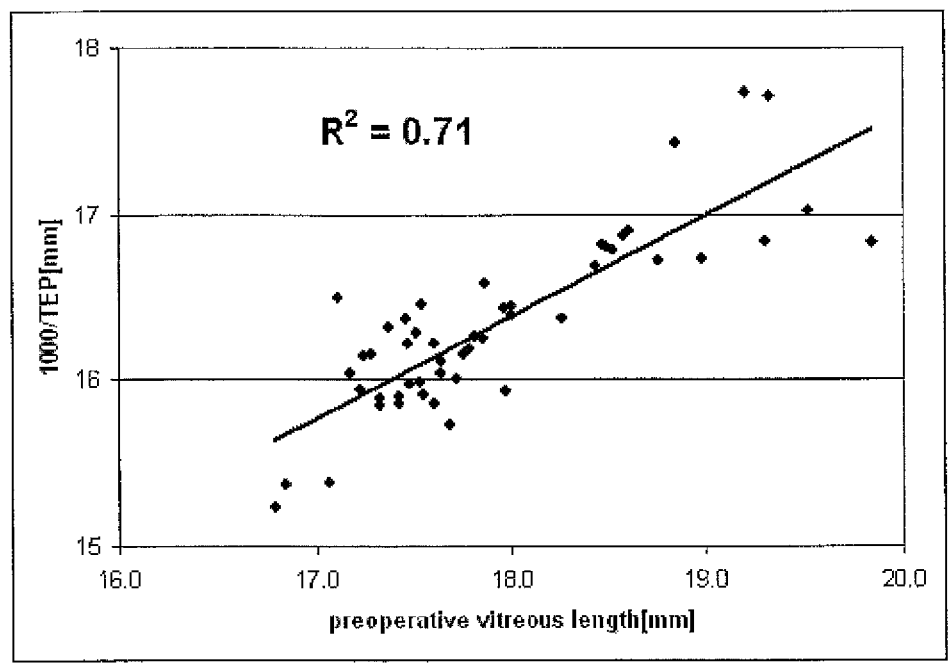
FIG. 5 is a graph illustrating the post operative total power of the eye versus the preoperative vitreous length.

As detailed in FIG. 5, the preoperative vitreous length was also found to be a good predictor for the post operative total power of the eye with $r^2$=0.71.

Each of the aforementioned constant values are preferably within plus or minus 20 percent of the nominal value thereof, or even more preferably within plus or minus 10 percent of the nominal value thereof.

Figure 6:
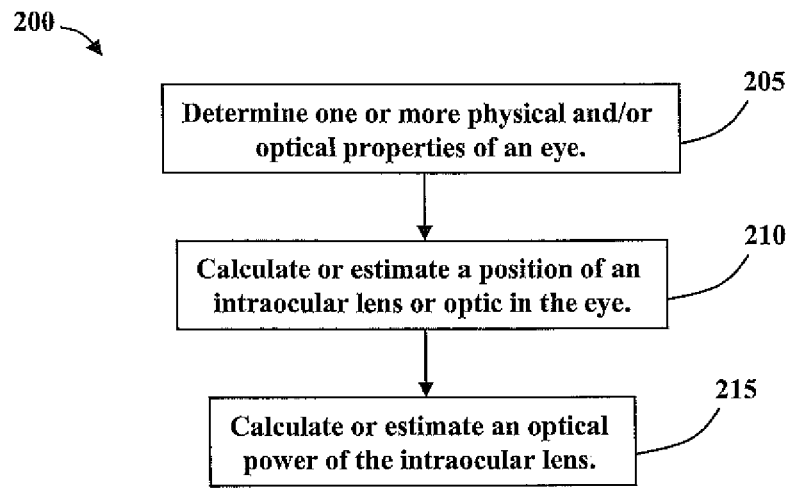
FIG. 6 is a flow chart of a method according to an embodiment of the present invention.
Figure 7:
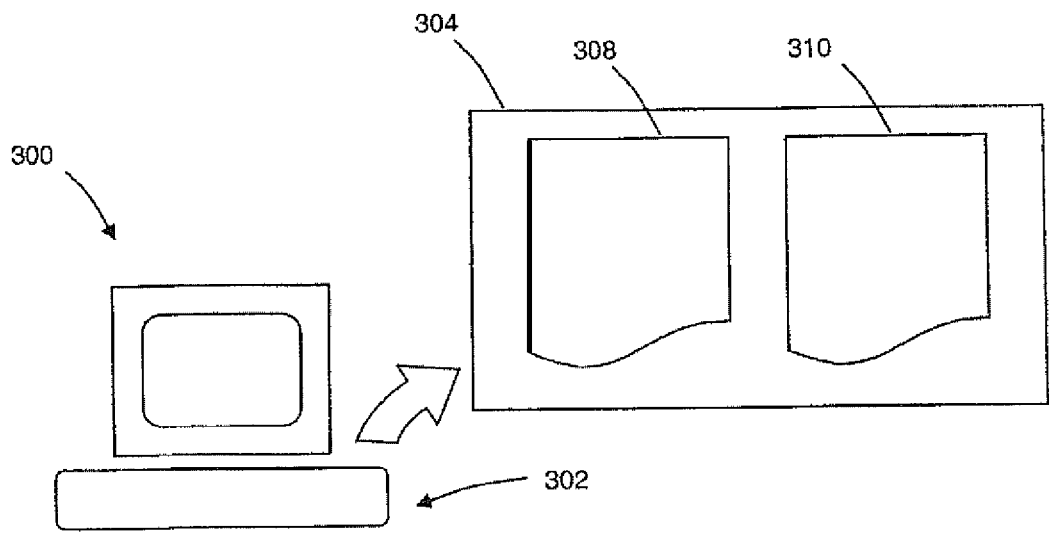
FIG. 7 is a graphical representation of the elements of computing system for selecting an ophthalmic lens according to an embodiment of the present invention.

Referring to FIG. 6, in certain embodiments, a method 200 for selecting the intraocular lens 100 or an optical power thereof comprises an element 205 of determining one or more physical and/or optical properties of the eye 100. The method 200 also comprises an element 210 of calculating a position of the intraocular lens 100 or the optic 102 after an ocular surgical procedure as detailed above. The method 200 additionally comprises an element 215 of calculating or estimating an optical power of the intraocular lens 100 suitable for providing a predetermined refractive outcome.

With reference to FIGS. 1 and 2, element 205 comprises measuring $ACD_{pre}$, AL, and/or LT of the eye 10 and then calculating $VL_{pre}$ from these measurements, as previously indicated. In addition, other various physical properties of the eye may also be measured or estimated (e.g., a refractive index of a material of the eye, and the like) and/or information of the patient or IOL collected (e.g., age, sex, which eye, IOL model, IOL optic and/or haptic dimensions and thickness, or the like).

The element 210 of the method 200 comprises calculating a position of the intraocular lens 100 or the optic 102 after an ocular surgical procedure. With reference to FIGS. 1 and 2, the calculated position of the intraocular lens 100 is based on measured or calculated values of $VL_{pre}$, $ACD_{pre}$, AL, and/or LT of the eye 10. These values may be used in one or more of the above equations to calculate the lens position. In certain embodiments, the constants are selected using regression routine, for example, based on a multiple linear regression (MLR) analysis or a partial least squares (PLS) regression analysis, which may be run for different IOL models.

The method 300 may be incorporated with one or more methods of inserting a lens within the individual eyes of the population. Such methods may also comprise making postoperative measurements of the eyes in the population to determine the postoperative position of the lens for each eye within the population and/or to use the information to further refine the mathematical modes defined by the equations above. Additionally or alternatively, such methods may further comprise conducting a statistical analysis of each measured or derived characteristic to determine (1) a correlation between the calculated postoperative lens position and the measured or derived characteristic(s) and/or (2) to determine coefficient value for an equation containing the measured or derived characteristic(s) as variables, the equation configured for calculating a postoperative lens position within an eye per IOL model.

Referring to FIG. 6, in certain embodiments, a computer system 300 for calculating a postoperative lens position within an eye and/or for selecting an ophthalmic lens or an optical power thereof comprises a processor 302 and a computer readable memory 304 coupled to the processor 302. The computer readable memory 304 has stored therein an array of ordered values 308 and sequences of instructions 310 which, when executed by the processor 302, cause the processor 302 to calculate a postoperative lens position within an eye and/or for selecting an ophthalmic lens or an optical power thereof. The array of ordered values 308 may comprise, for example, one or more ocular dimensions of an eye or plurality of eyes from a database, a desired refractive outcome, parameters of an eye model based on one or more characteristics of at least one eye, and data related to an IOL or set of IOLs such as a power, an aspheric profile, and/or a lens plane. In some embodiments, the sequence of instructions 310 includes determining a position of an IOL, performing one or more calculations to determine a predicted refractive outcome based on an eye model and a ray tracing algorithm, comparing a predicted refractive outcome to a desired refractive outcome, and based on the comparison, repeating the calculation with an IOL having at least one of a different power and/or a different IOL location.

The computer system 300 may be a general purpose desktop or laptop computer or may comprise hardware specifically configured performing the desired calculations. In some embodiments, the computer system 300 is configured to be electronically coupled to another device such as a phacoemulsification console or one or more instruments for obtaining measurements of an eye or a plurality of eyes. In other embodiments, the computer system 300 is a handheld device that may be adapted to be electronically coupled to one of the devices just listed. In yet other embodiments, the computer system 300 is, or is part of, refractive planner configured to provide one or more suitable intraocular lenses for implantation based on physical, structural, and/or geometric characteristics of an eye, and based on other characteristics of a patient or patient history, such as the age of a patient, medical history, history of ocular procedures, life preferences, and the like.

Generally, the instructions of the system 300 will include elements of the method 300 and/or parameters and routines for performing calculations of one or more of Equations above.

In certain embodiments, the system 300 includes or is part a phacoemulsification system, laser treatment system, optical diagnostic instrument (e.g, autorefractor, aberrometer, and/or corneal topographer, or the like). For example, the computer readable memory 304 may additionally contain instructions for controlling the handpiece of a phacoemulsification system or similar surgical system. Additionally or alternatively, the computer readable memory 304 may additionally contain instructions for controlling or exchanging data with an autorefractor, aberrometer, and/or corneal topographer, or the like, In some embodiments, the system 300 includes or is part of a refractive planner. The refractive planner may be a system for determining one or more treatment options for a subject based on such parameters as patient age, family history, vision preferences (e.g., near, intermediate, distant vision), activity type/level, past surgical procedures.

The above presents a description of the best mode contemplated of carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above which are fully equivalent. Consequently, it is not the intention to limit this invention to the particular embodiments disclosed. On the contrary, the intention is to cover modifications and alternate constructions coming within the spirit and scope of the invention as generally expressed by the following claims, which particularly point out and distinctly claim the subject matter of the invention.

What is claimed is:

1. A method of selecting an intraocular lens or an optical power thereof, comprising:
    determining, by a processor, a value for the postoperative vitreous length of an eye from preoperative measurements selected from the group consisting of: $VL_{pre}$, $ACD_{pre}$, and LT; AL, $ACD_{pre}$, and LT; and $VL_{pre}$ and LT; calculating, by the processor, an optical power of the intraocular lens based on the postoperative vitreous length suitable for providing a predetermined refractive outcome; wherein $VL_{pre}$ is the preoperative vitreous length of the eye measured as the difference between the axial length and the anterior chamber depth prior to surgery plus the lens thickness, $ACD_{pre}$ is anterior chamber depth prior to surgery, LT is the lens thickness, and AL is the axial length.

2. The method of claim 1, wherein the postoperative vitreous length is a dependent variable $VL_{post}$ and the mathematical relationship is:

$$VL_{post}=C1+C2*VL_{pre}+C3*ACD_{pre}+C4*LT.$$

3. The method of claim 2, wherein C1 is a constant with a nominal value of −0.901, C2 is a constant with a nominal value of 0.982, C3 is a constant with a nominal value of 0.309, and C4 is a constant with a nominal value of 0.545, each of the constants having a value that is within plus or minus 20 percent of the nominal value thereof.

4. The method of claim 3, wherein each of the constants has a value that is within plus or minus 10 percent of the nominal value thereof.

5. The method of claim 3, wherein each of the constants has a value that is within plus or minus 5 percent of the nominal value thereof.

6. The method of claim 1, wherein the postoperative vitreous length is a dependent variable $VL_{post}$ and the mathematical relationship is:

$$VL_{post}=AL-(ACD_{pre}+0.5LT).$$

7. The method of claim 1, wherein the postoperative vitreous length is a dependent variable $VL_{post}$ and the mathematical relationship is:

$$VL_{post}=-C1+C2*VL_{pre}+C3*LT.$$

8. The method of claim 7, wherein C1 is a constant with a nominal value of 1.63, C2 is a constant with a nominal value of 0.912, and C3 is a constant with a nominal value of 0.448, each of the constants having a value that is within plus or minus 20 percent of the nominal value thereof.

9. The method of claim 8, wherein each of the constants has a value that is within plus or minus 10 percent of the nominal value thereof.

10. The method of claim 8, wherein each of the constants has a value that is within plus or minus 5 percent of the nominal value thereof.

11. A system for providing an intraocular lens, the system comprising:
a processor; and
a computer readable memory configured to communicate with the processor, the memory having stored therein:
an array of ordered values, including at least one of:
one or more ocular dimensions, the ocular dimensions including $VL_{pre}$, $ACD_{pre}$, and LT;
a predetermined refractive outcome;
a sequence of instructions which, when executed by the processor, cause the processor to select an intraocular lens or an intraocular lens power, the sequence of instructions including:
calculating the $VL_{post}$;
calculating an optical power of the intraocular lens suitable for providing the predetermined refractive outcome,
wherein $VL_{pre}$ is the preoperative vitreous length of the eye measured as the difference between the axial length and the anterior chamber depth prior to surgery plus the lens thickness, $ACD_{pre}$ is anterior chamber depth prior to surgery, LT is the lens thickness, and $VL_{post}$ is the postoperative vitreous length.

12. The system of claim 11, wherein $VL_{post}$ is a dependent variable and the mathematical relationship is:

$$VL_{post}=C1+C2*VL_{pre}+C3*ACD_{pre}+C4*LT.$$

13. A system for providing an intraocular lens, the system comprising:
a processor; and
a computer readable memory configured to communicate with the processor, the memory having stored therein:
an array of ordered values, including at least one of:
one or more ocular dimensions, the ocular dimensions including AL, $ACD_{pre}$, and LT;
a predetermined refractive outcome;
a sequence of instructions which, when executed by the processor, cause the processor to select an intraocular lens or an intraocular lens power, the sequence of instructions including:
calculating the $VL_{post}$;
calculating an optical power of the intraocular lens suitable for providing the predetermined refractive outcome,
wherein AL is the axial length, $ACD_{pre}$ is anterior chamber depth prior to surgery, and LT is the lens thickness, and wherein $VL_{post}$ is a dependent variable and the mathematical relationship is:

$$VL_{post}=AL-(ACD_{pre}+0.5LT).$$

14. A system for providing an intraocular lens, the system comprising:
a processor; and
a computer readable memory configured to communicate with the processor, the memory having stored therein:
an array of ordered values, including at least one of:
one or more ocular dimensions, the ocular dimensions including $VL_{pre}$ and LT;
a predetermined refractive outcome;
a sequence of instructions which, when executed by the processor, cause the processor to select an intraocular lens or an intraocular lens power, the sequence of instructions including:
calculating the $VL_{post}$;
calculating an optical power of the intraocular lens suitable for providing the predetermined refractive outcome,
wherein $VL_{pre}$ is the preoperative vitreous length of the eye measured as the difference between the axial length and the anterior chamber depth prior to surgery plus the lens thickness, and LT is the lens thickness, and $VL_{post}$ is the postoperative vitreous length, and wherein $VL_{post}$ is a dependent variable and the mathematical relationship is:

$$VL_{post}=-C1+C2*VL_{pre}+C3*LT.$$

* * * * *